(12) United States Patent
MacHattie et al.

(10) Patent No.: US 7,609,366 B2
(45) Date of Patent: Oct. 27, 2009

(54) MATERIAL MEASUREMENT SYSTEM FOR OBTAINING COINCIDENT PROPERTIES AND RELATED METHOD

(75) Inventors: Ross MacHattie, Mississauga (CA); Frank M. Haran, Vancouver (CA); Graham I. Duck, Vancouver (CA); David R. Jez, Vancouver (CA); Dan Gordon, Vancouver (CA)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/941,574

(22) Filed: Nov. 16, 2007

(65) Prior Publication Data

US 2009/0128799 A1    May 21, 2009

(51) Int. Cl.
*G01C 3/08* (2006.01)
(52) U.S. Cl. .............. 356/5.05; 356/5.01; 356/4.01; 162/49; 162/198; 162/263
(58) Field of Classification Search ........... 356/3.01–22
See application file for complete search history.

(56) References Cited

U.S. PATENT DOCUMENTS

| | | | |
|---|---|---|---|
| 4,879,471 A | 11/1989 | Dahlquist | |
| 5,659,392 A | 8/1997 | Marcus et al. | |
| 6,627,043 B1 | 9/2003 | Mantylia | |
| 2005/0030520 A1* | 2/2005 | Wada et al. | 356/28.5 |
| 2006/0132796 A1* | 6/2006 | Haran | 356/503 |
| 2006/0243931 A1* | 11/2006 | Haran et al. | 250/574 |
| 2007/0137823 A1* | 6/2007 | Haran | 162/198 |
| 2007/0235658 A1* | 10/2007 | Zimdars et al. | 250/390.07 |
| 2008/0179528 A1 | 7/2008 | Demers | |

* cited by examiner

*Primary Examiner*—Thomas H Tarcza
*Assistant Examiner*—Luke D Ratcliffe
(74) *Attorney, Agent, or Firm*—Patents On Demand, P.A.; Neil R. Jetter

(57) ABSTRACT

A material measurement system (500) includes a THz generator including at least one laser source (111) for emitting optical pulses, the optical pulses coupled to a THz emitter (51) operable for emitting pulsed THz radiation at a sample location on material while being processed (14) by a manufacturing system. A receiver (52) is operable to receive the optical pulses and to detect reflected or transmitted THz radiation from the sample location (14) synchronously with the optical pulses and provide electrical detection signals. Synchronizing optics (112, 113, 114) is operable to receive the optical pulses from said laser and provide the optical pulses to both the receiver (52) and the THz emitter (51). A controller (25) includes at least one processor (87) for receiving the electrical detection signals and providing a processed electrical detection signal, and an analyzer (88) operable to determine at least one, and generally a plurality of properties of the material from the processed electrical detection signal.

20 Claims, 5 Drawing Sheets

MATERIAL MEASUREMENT SYSTEM FOR OBTAINING COINCIDENT PROPERTIES AND RELATED METHOD

FIELD OF THE INVENTION

The invention generally relates to process control systems and more specifically to Terahertz spectroscopy-based measurement and control systems for controlling the quality of manufactured materials, such as paper.

BACKGROUND

Processing facilities, such as paper-making mills and material manufacturing mills, are typically managed using process control systems and quality control systems (QCS). Valves, pumps, motors, heating/cooling devices, and other industrial equipment and electronics typically perform actions needed to process materials in the processing facilities. Among other functions, the process control systems and QCS often manage the use of the industrial equipment in the processing facilities.

The process control system may comprise a Distributed Control Systems (DCS). The DCS is typically connected to and works in coordination with the QCS which generally include devices for measuring attributes of the product being manufactured (e.g. paper), and for sending control signals to the industrial equipment to adjust the quality of the product they are manufacturing.

Controllers are often used to control the operation of the industrial equipment in the processing facilities. The controllers typically monitor the operation of the industrial equipment, provide control signals to the industrial equipment, and/or generate alarms when malfunctions are detected. The field devices can include sensors (e.g., temperature, pressure and flow rate sensors), as well as other passive and/or active devices. Process controllers can receive process information, such as field measurements made by the field devices, in order to implement a control routine. Control signals can then be generated and sent to the industrial equipment to control the operation of the process and the manufacture of materials.

In the manufacture of paper, for example, a number of field devices are known to be utilized for measuring the moisture content and the temperature of the paper during the paper-making process. In the process, a web of paper is formed from an aqueous suspension of fibers (stock) on a traveling mesh papermaking fabric. Water in the paper drains by gravity and suction through the fabric. The web is then transferred to a pressing section where more water is removed by pressure and vacuum. The web next enters the dryer section where steam heated dryers and hot air completes the drying process. The paper machine is, in essence, a water removal system.

A typical forming section of a paper-making system includes an essentially endless traveling papermaking fabric or wire, which travels over a series of water removal elements such as table rolls, foils, vacuum foils, and suction boxes. The stock is carried on the top surface of the papermaking fabric and is de-watered as the stock travels over the successive de-watering elements to form a sheet of paper. The wet sheet is then transferred to the press section of the paper-making system where enough water is removed to form a sheet of paper. Many factors influence the rate at which water is removed which ultimately affects the quality of the paper produced.

On-line measurements made during the paper-making process generally include basis weight, moisture, and sheet caliper, i.e., thickness. The measurements can be used for controlling process variables with the goal of maintaining output quality and thus minimizing the quantity of product that is rejected. The on-line sheet property measurements are often accomplished by scanning sensors that periodically traverse the sheet material from edge to edge.

Referring to FIG. 1, a known scanning device 17 shown is used to traverse the sheet material (e.g., paper 14) from edge to edge and take one or more property measurements of the sheet material during the paper-making process. Scanning device 17 includes multiple sensors S1, S2, and S3 that are arranged adjacent to one another. The sensors are distinct from one another since each sensor uses its own specific hardware to measure a specific property of the sheet material. Each specific property generally requires a different measurement technology. For example, S1 may be an Infra-Red (IR) sensor to measure moisture at location P1, S2 may be a nuclear element to measure basis weight at location P2, and S3 may be an optical unit for measuring another material property at location P3.

The scanning device 17 is generally placed at the "dry" end of the paper-making process where the sensors are not exposed to high temperatures or high humidity conditions, such as the extreme conditions associated with a "wet-end", for example, near a steam box. The sensors S1, S2 and S3 of the scanning device 17 are on the dry end because their on-board electronics may not operate properly, or can be damaged, in the high heat and moisture environments at the "wet-end". Furthermore, the sensors S1, S2 and S3 together are generally bulky in size and cannot easily fit, or be placed, at strategic measuring locations within the "wet-end". Accordingly, the "dry-end" of the paper-making process is generally used for taking property measurements of the sheet material during the paper-making process.

A control system used to monitor the paper-making process can assess the paper properties measured at the different locations P1, P2 and P3 at the "dry-end", and control process parameters based on these "final" measurements. Actuation of systems at the wet end, press, dryer, and finishing sections of a paper machine are typically all controlled by readings from the "dry-end" scanner at the reel. For example, it is conventional to measure the moisture content of sheet material upon it leaving the main dryer section, or measure the moisture content at the take-up reel employing the scanning sensors at the "dry-end". The measurements at the "dry-end" can be used to adjust the machine operation of the paper-making process to achieve desired parameters and performance.

While "dry-end" measurement control has provided significant benefits to the paper manufacturing industry, it does have certain limitations. For instance, the traditional scanning device, such as scanning device 17 shown in FIG. 1, may not be able to accurately measure basis weight or caliper due to the differences in location (P1, P2 and P3) of the respective measurements on the paper 14. Although the sensors are proximate to one another, they are generally unable to measure discrete quality properties at a particular location simultaneously. Moreover, the scanning device may not be able to take measurements at different points in the process, for example, at the "wet-end" where extremely high temperature and moisture conditions exist, which as previously noted can result in damage to the receiving sensors (S1, S2 and S3).

The "dry-end" measurements are generally inadequate for capturing the changes of the paper at different process points in the paper-making process. Such incomplete process measurements can result in manufacturing deficiencies, such as lower quality and higher cost. Moreover, when measurements taken at the "dry-end" in the paper-making process are used to estimate measurements at the "wet-end", errors can be introduced as a result of the estimation. For example, the measurements may not be from the same spot of paper, thus the errors may not be due to the same processes. Errors can also be generated due to machine speed inaccuracies, different measurement spot sizes, non-linear shrinkage and/or sheet wander. Furthermore, traditional scanning devices operating at the "dry-end" have difficulty separating densification in the press section from that in the dryer sections, and thus cannot generally provide accurate measurements of paper density.

SUMMARY

The Summary is provided to comply with 37 C.F.R. §1.73, requiring a summary of the invention briefly indicating the nature and substance of the invention. It is submitted with the understanding that it will not be used to interpret or limit the scope or meaning of the claims.

A material measurement system includes a THz generator including at least one laser source for emitting optical pulses, the optical pulses coupled to a THz emitter operable for emitting pulsed THz radiation at a sample location on material while being processed by a manufacturing system. A receiver is operable to receive the optical pulses and to detect reflected or transmitted THz radiation from the sample location synchronously with the optical pulses and provide electrical detection signals. Synchronizing optics is operable to receive the optical pulses from the laser and provide the optical pulses to both the receiver and the THz emitter. A controller includes at least one processor for receiving the electrical detection signals and providing a processed electrical detection signal. An analyzer is operable to determine at least one (and generally a plurality) property of the material from the processed electrical detection signal.

In one embodiment of the invention the THz emitter emits pulsed THz radiation and the analyzer is operable to generate a time-domain spectroscopy (TDS) spectrum from the processed electrical detection signal. In embodiments of the invention the controller and laser are remotely located from the manufacturing system. As used herein, "remotely located" refers to an element that is located at the side of the machine at the closest and in another room near the paper machine at the farthest, typically being one to fifty meters away from the machine. The controller can comprise a multi-variable controller.

The THz emitter and receiver can be combined in a single sensor module. In this embodiment, the system can further comprise a scanner coupled to the sensor module for moving the sensor to obtain the properties of the sheet material from a plurality of sample locations across a width of the system. The analyzer can be operable to simultaneously measure two or more of basis weight, moisture, and caliper (thickness), composition, and fiber orientation at the sample location.

A controlled system or forming material comprises a material making system including a plurality of actuators. A control system is operatively coupled to the material making system comprising a THz generator including at least one laser source for emitting optical pulses, the optical pulses coupled to a THz emitter operable for emitting pulsed THz radiation at a sample location on material being processed by the material masking system. A receiver is operable to receive the optical pulses and to detect reflected or transmitted THz radiation from the sample location synchronously with the optical pulses and provide electrical detection signals. Synchronizing optics is operable to receive the optical pulses from the laser and provide the optical pulses to both the receiver and THz emitter. A controller comprising at least one processor receives the electrical detection signals and provides a processed electrical detection signal. An analyzer is operable to determine at least one property of the material from the processed electrical detection signal. The controller is operably linked to control operation of the material making system using at least one of the plurality of actuators based on the property.

In one embodiment the material making system can comprise a paper making system comprising in serial connection a press section including at least one actuator arranged to control mechanical water removal from wetstock material to begin formation of a sheet material, a dryer section including at least one actuator arranged to control evaporative drying of the sheet material, a calendering stack including at least one actuator to control compressive pressure to the sheet material, and a take-up reel for producing a continuous roll of the sheet material.

A method for in-situ quality control of material processed by a manufacturing system, comprises the steps of directing THz radiation at a sample location on material being processed by the manufacturing system, measuring reflected radiation or transmitted radiation from the sample location and generating electrical detection signals therefrom, transmitting the electrical detection signals to a remotely located controller comprising at least one processor for receiving the electrical detection signals, and providing a processed electrical detection signal. At least one property of the material is determined from the processed electrical detection signal, and at least one process parameter is automatically modified based on the property. The at least one property can comprises a plurality of the properties, wherein the plurality of properties are determined from coincident measuring of the reflected radiation or transmitted radiation from a single sample location. The determining step can comprise generating a time-domain spectroscopy (TDS) spectrum from the processed electrical detection signal.

The sample location can be within a wet-zone of the system. The Wet-zone is defined herein as an area where there is more water than fiber (by weight). Generally, dry end measurements refer to measurements where there is less water than fiber, such as less than 20% moisture.

DETAILED DESCRIPTION OF TEE INVENTION

Figure 1:
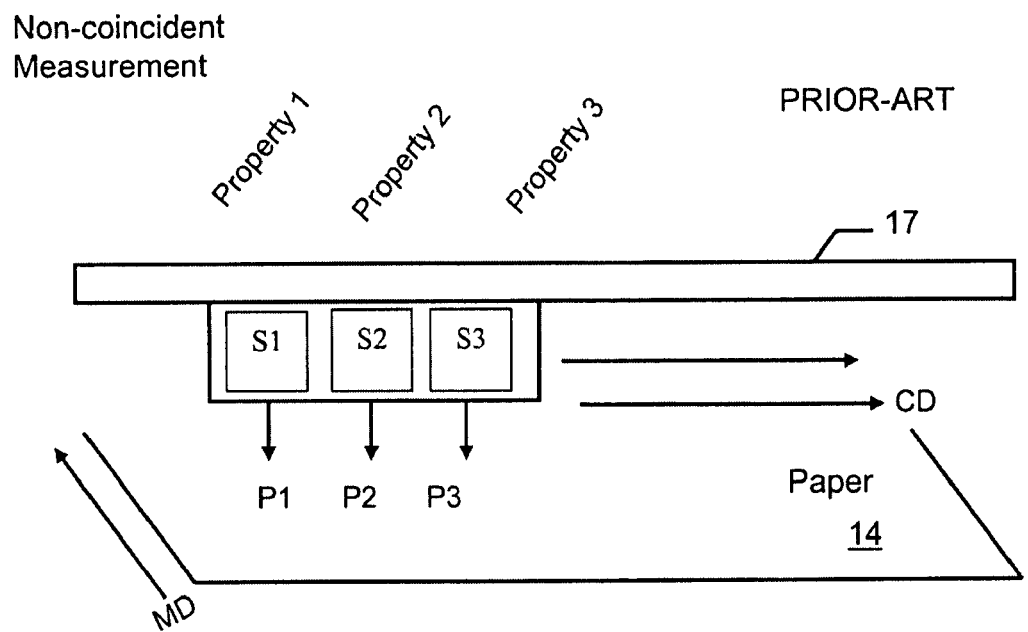
FIG. 1 is a schematic illustration of a known sensor device comprising a plurality of separate sensors for measuring one or more paper properties at different locations on the paper.
Figure 2:
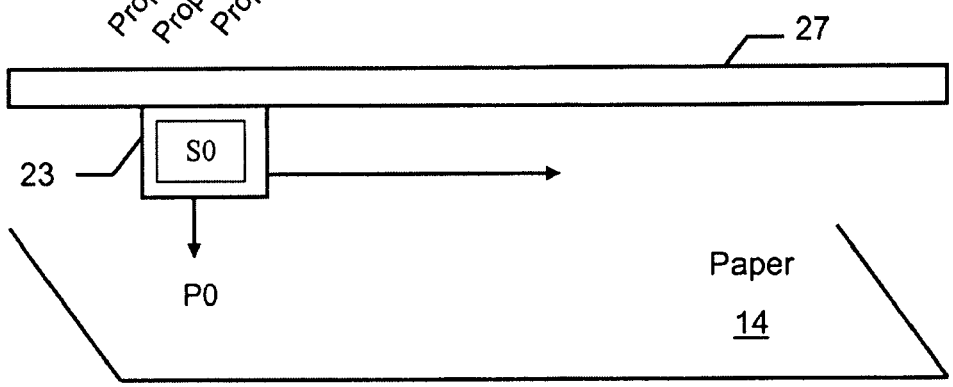
FIG. 2 is a schematic illustration of an exemplary sensor device for simultaneously measuring multiple paper properties at a coincident location on the paper, according to an embodiment of the present invention.

Referring FIG. 2, an exemplary sensor device 23, according to an embodiment of the invention for simultaneously measuring at least one property, and generally a plurality of properties, of a material, such as paper 14, is shown. In one arrangement, the sensor device 23 can be coupled to a scanner 27 operable to move the sensor device 23 across the width of the paper, transverse to the paper translation path. In another arrangement, the sensor device 23 can remain at a fixed location along the length of the scanner 27 for obtaining fixed point measurements. In the fixed embodiment, the mounting device for the sensor generally does not span the entire width of the machine, but generally projects a meter or two from one edge. The sensor device 23 can obtain a plurality of property measurements of the paper 14 coincidently; that is, at the same paper location and at the same time. For example, the sensor device 23 can measure Property 1, Property 2, and Property 3, such as basis weight, moisture content, fiber orientation and caliper at the same paper location shown, P0, at the same time. As used herein the "same time" refers to a time interval of generally no more than 10 milli-seconds. Terahertz radiation is used for the property measurements. In one embodiment Terahertz/Time Domain Spectroscopy (THz/TDS) is employed.

As known in the art, terahertz time-domain spectroscopy (THz-TDS) is a spectroscopic technique where a unique generation and detection scheme is used to probe material properties with short pulses of THz radiation. The generation and detection scheme has been found by the present Inventors to be sensitive to the effect of the material, such as a sheet-material, on both the amplitude and the phase of the THz radiation.

The THz region is sometimes also referred to as the far-infrared or the sub-millimeter region, and lies between the infrared (IR) region and the microwave region of the electromagnetic spectrum. The boundaries of the THz region are not exactly defined but are generally taken to lie between 30 μm and 1500 μm wavelength, or 10 THz and 0.2 THz frequency, or 330 $cm^{-1}$ and 7 $cm^{-1}$ wavenumber.

The scanner 27 and sensor device 23 are suitable for use in material manufacturing processes, such as sheet-material manufacturing processes. One example is papermaking system for producing a continuous sheet of paper 14, such as system 300 according to an embodiment of the invention illustrated in FIG. 3. The paper-making system 300 shown includes a head box 32, a steam box 28, a calendaring stack 30, a take-up reel 48, a scanner system 20 at the "dry-end" and the scanner 27 including the coincident sensor device 23 at the "wet-end". Sensor device 23 generally comprises a THz emitter and THz receiver. Although shown as separate modules, the scanner 27 and sensor device 23 can be integrated with, or replace, the scanner 20. In the head box 32, actuators are arranged to control discharge of wet stock onto supporting wire 36. The sheet of fibrous material that forms on top of the wire 36 is trained to travel in the machine direction between rollers 34 and 38 and passes through a calendering stack 30. The sheet-material can be in the form of a film, web, or sheet.

The calender stack 30 includes actuators that control the compressive pressure applied across the paper web. The paper-making system 300 also includes a press section (not shown) before stack 30 where water is mechanically removed from the sheet and where the web is consolidated. Thereafter, water is removed by evaporation in the dryer section (not shown). The finished sheet product 14 is collected on a reel 48. The dashed line shown in FIG. 3 separates the wet-end from the dry-end. The boundary between the respective wet and dry ends as used herein refers to shortly after the stack 30, in the early dryer section, where the fiber content first starts to surpass the moisture content.

Scanner 20 generally includes pairs of horizontally extending guide tracks 24 that span the width of the paper 14. The guide tracks are supported at their opposite ends by upstanding stanchions 22 and are spaced apart vertically by a distance sufficient to allow clearance for paper 14 to travel between the tracks. A conventional sensor 26 is secured to a carriage 24 that moves back-and-forth over the paper 14 as measurements are made. Sensor 26 can be used to measure final quality (e.g. basis weight, moisture, caliper). Sensor 23 might be added to a system that already has sensor 26, or sensor 23 could replace sensor 26. Sensor 26 could be one sensor measuring one property, or it could be several distinct sensors measuring several properties. Scanner 27 can include pairs of horizontally extending guide tracks (not shown) that span the width of the paper 14. The sensor 23 can also be secured to a small carriage (not shown) on the scanner 27 that moves back-and-forth over the paper 14 as measurements are made. A fiber optic cable 39 is one means for communication that can communicably connect THz/TDS optoelectronics 110 that is remotely located from the sensor device 23 (and the paper making components of system 300). THz/TDS optoelectronics device 110 comprises a laser system and synchronization optics as described below. Fiber optic cable 39 can be used to route to couple optical pulses from the laser to sensor 23 including located proximate to the paper making components of system 300.

Optoelectronics is communicably connected to an associated controller which is also remotely located from system 300 (not shown in FIG. 3; see FIG. 5 described below). In such an arrangement, neither the sensitive electronic components of the THz/TDS optoelectronics device 110 nor the controller are exposed to the extremely high temperatures and moisture conditions of the "wet-end" of system 300.

Figure 3:
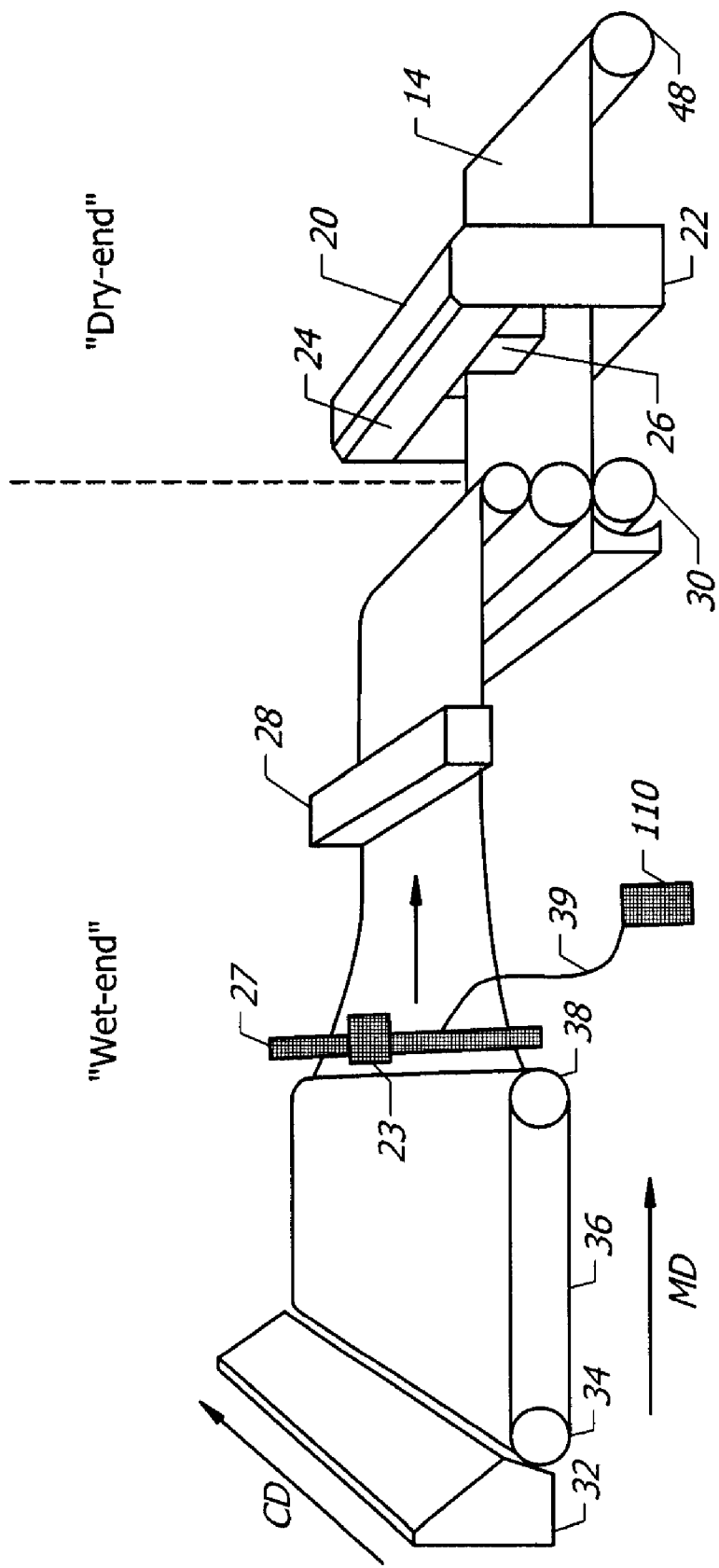
FIG. 3 is a schematic illustration of an exemplary paper-making system incorporating the sensor device of FIG. 2, according to an embodiment of the present invention.

As shown in FIG. 3, the sensor device 23 is placed at the "wet-end" of the paper-making process on the scanner 27. In another arrangement, the sensor device 23 can also be placed near the steam box 28 where temperatures and humidity are exceedingly high compared to conditions at the "dry-end". The sensor device 23 can also be placed near the head box 32, or any other components in proximity to the "wet-end". In another embodiment, sensor device 23 is placed at the dry end of system 300. The scanner 27, sensor device 23 and fiber optic cable 39 alone or in combination are generally sufficiently flexible and small enough to be located anywhere within space constrained regions of the paper-making system 300.

The sensor device 23 deployed in the "wet-end" permits measurement of "wet-end" conditions that allow measurement of primary paper quality parameters simultaneously at a single paper location. The small rugged form factor possible for sensor device 23 allows the measurements to be placed at the source of disturbance, allowing controls and actuators to correct problems associated with the paper-making process at a specific time. In another embodiment, multiple sensor devices 23 can also be placed at various locations within the paper-making system 300 to each measure multiple paper quality parameters at coincident locations within the paper-making system 300.

Figure 4:
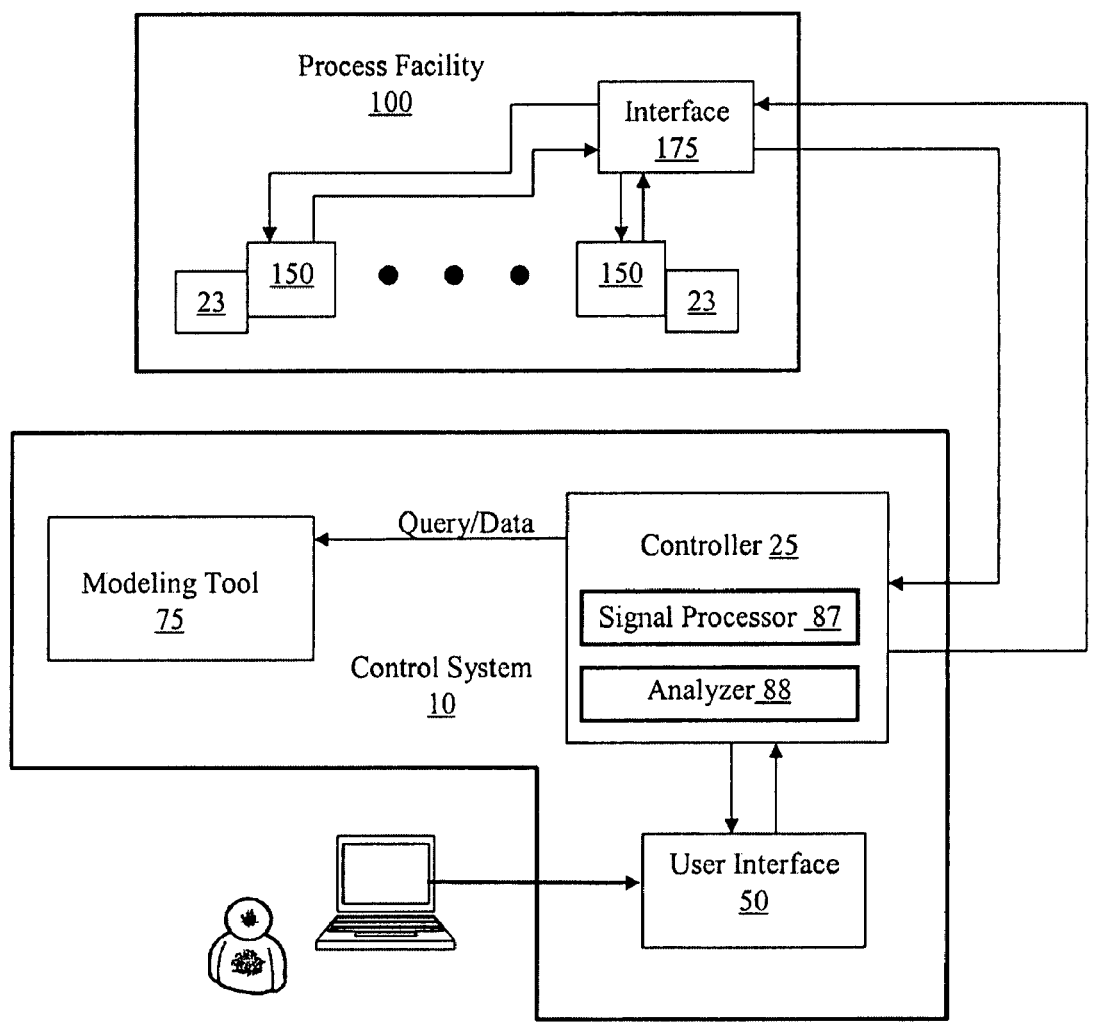
FIG. 4 is a schematic illustration of an exemplary paper-making system including a THz-spectroscopy based control system for process control, according to an embodiment of the present invention.

Referring to FIG. 4, a schematic illustration of an exemplary control system 10 for process control is shown according to an embodiment of the invention. Control system 10 includes a controller 25 which comprises a user interface 50, and a modeling tool 75. The controller 25 is shown including a processor (e.g. signal processor) 87 and an analyzer 88. Control system 10 can include other components, and combinations of components that can receive and/or retrieve operational parameters; retrieve, receive and/or generate paper-process models, and/or implement control with respect to one or more paper processes or systems. Controller 25, the user interface 50, and the modeling tool 75 can be separate components or can be integrated with each other, such as in a single processor or computer.

The controller 25 is shown coupled to, or in communication with, one or more control devices 150 of a process facility 100, for example control devices associated with the paper-making system of FIG. 3, such as through use of an interface 175. The coupling or communication can be through use of various components and known techniques, including hardwire, optical and/or wireless couplings. Control system 10 can be in direct communication with one or more of the control devices 150 associated with the paper-making process, such as directly controlling each of the devices or in a master-slave configuration of devices. Although not shown, control system 10 can be coupled to the process facility 100 by way of an application server.

The control devices 150 can be various devices integrated into the process of facility 100, including valves, pumps, motors, heating/cooling devices, and other industrial equipment, as well as sensors (e.g., temperature, pressure, and flow rate sensors), and other passive and/or active devices. For example, the control devices 150 can correspond to controls associated with the head box 32, steam box 28, calendering stack 30, take-up reel 48, scanner system 20, scanner 27 or other components of the paper-making system 300 of FIG. 3, such as a cooling apparatus or heating apparatus. The present invention is not limited by the type of control devices that are used to implement the control of the process, and can include a variety of devices and combinations of devices, such as a sub-system to adjust pressure and/or temperature in a portion of the process.

The interface 175 can couple one or more sensor devices 23 to the one or more control devices 150 to each measure one or more properties of a sheet-material, such as paper, coincidently during the manufacturing process. In practice, the controller 25 can be operably coupled to the interface 175 to evaluate the multiple paper quality parameters using at least in part THz spectroscopy. Each property under observation can invoke various degrees of control complexity. The controller 25 can also actuate the one or more control devices 150 of the process facility 100 to control the paper-making process in view of the measured paper quality properties to optimize process efficiency and cost.

In one inventive aspect, controller 25 monitors a paper-making process and target a moisture profile from forming to pressing to drying to finishing. The controller 25 receives electrical detection signals from the THz receiver component of sensor device 23 during the paper-making process. The controller 25 can process the electrical detection signals and through analysis determine or more paper quality properties to determine, for example, how the moisture profile achieved, and how the moisture profile should be updated during the paper-making process from "wet-end"-to-press and press-to-dryers at the "dry-end". As known in the art, the moisture profile can have significant impact on variables such as sheet tension profiles, sheet breaks, shrinkage, winder efficiency, pressroom operation.

The modeling tool 75 shown in FIG. 4 can evaluate the paper quality property and target a moisture profile during process to predict control settings that achieve optimal cost savings. The modeling tool 75 can also predict changes in paper quality in view of the quality properties measured by coincident sensor device 23, and propose to the operator control adjustments that reduce cost for higher efficiency. The user interface 50 can present the one or more measured paper quality parameters, and receive one or more control commands for adjusting an actuation of the one or more control devices 150. As an example, the controller 25 can monitor quality properties measured by coincident sensor device 23 to control the cross direction (CD) weight profile on dilution flow control head boxes 32. Such control could otherwise be problematic if web wander and non-linear shrinkage change the mapping of measurement zones to actuator zones were not taken into account at the "wet-end". Monitoring of the quality properties coincidently in the "wet-end" also provides separation of machine direction (MD) and CD variation components.

Notably, the measurement of a plurality of properties at a single paper location can help suppress errors associated with formation variations. For example, each control device 150 can be equipped with a coincident sensor device 23 to simultaneously measure multiple paper quality properties. In such regard, control loops can be formed around the major paper machine sub-processes of dryer, press and "wet-end" components. The controller 25 can evaluate the paper-quality properties and suppress or remove paper quality variations at their source, and enable efficient, good for the paper quality paths to be targeted and reproduced. This can provide a significant improvement in paper machine control over current reel scanner centric models where the sensing elements at the "dry-end" are not sufficiently rugged or flexible enough to operate at the "wet-end", nor sufficiently capable of obtaining coincident measurements at a same location on the paper 14.

The control system 10 can include associated writeable memory, which is preferably non-volatile, to serve as a data repository for various variables, data or other information, such as storing operational variables that have been determined based upon operational parameters that were calculated, simulated, measured, or otherwise sensed from the process being controlled. The memory can be part of the controller 25, modeling tool 75, and/or another component of the control system 10, such as for storing the models provided by the modeling tool.

Figure 5:
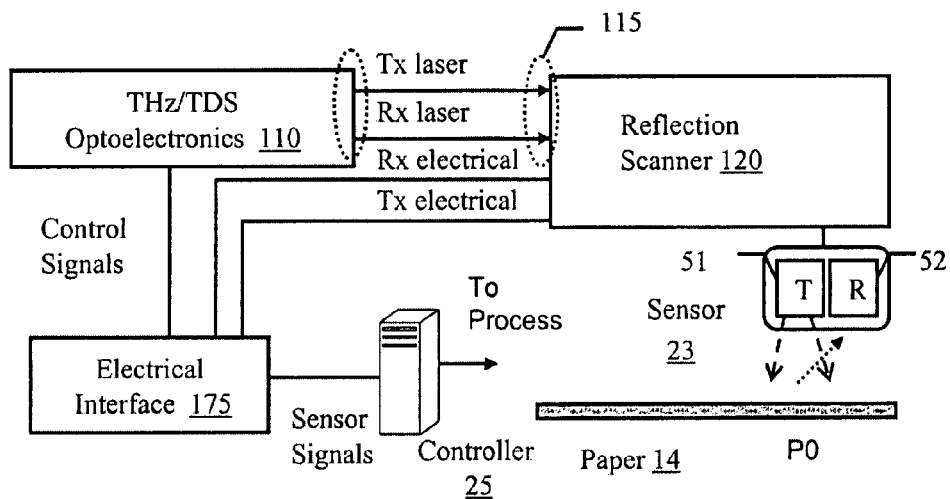
FIG. 5 is a schematic illustration of an exemplary high-speed fiber optic reflection scanning system incorporating the sensor device of FIG. 2, according to an embodiment of the present invention.

Now referring to FIG. 5, a schematic illustration of an exemplary terahertz time-domain spectroscopy (THz-TDS)-based measurement system 500 according to an embodiment of the invention for coincidentally measuring one or more properties of a sheet material, such as paper 14, during a sheet material manufacturing process is shown. The system 500 shown includes controller 25, a TeraHertz/Time Domain Spectroscopy (THz/TDS) optoelectronic device 110 comprising a laser and synchronization optics, an electrical interface 175, and a scanner 120 coupled to sensor device 23. The sensor device 23 can include a THz transmitting sensor head 51 (T) and a THz receiver 52 (R). In one embodiment a THz transceiver provides both the THz transmitting sensor head 51 (T) and THz receiver 52 (R). In practice, as described above, sensor device 23 can be positioned at sample location within a "wet-end" of the sheet material being processed, while THz/TDS optoelectronics 110 is disposed remote from the wet end.

Briefly, THz/TDS optoelectronics 110 includes a laser source (not shown) that generates very short laser pulses (e.g. pulses that last on the order of a femtosecond). The pulsed laser signal is conveyed through the transmission laser path of the fiber optic link 115 from the remotely located THz/TDS optoelectronic device 110 to the sensor head 51 at the sample location in the "wet-end". The THz sensor head 51 generally contains a semi-conducting material that generates a THz radiation pulse when exposed to the pulsed laser signal. The THz radiation pulse is directed to the sample location, P0. The ultra-short laser signals are conveyed through the Rx laser path of the fiber optic link 115 from the THz/TDS optoelectronic device 110 to the THz receiver 52. The ultra-short laser signals establish when the THz receiver 52 measures a portion of an electric field of THz radiation emanating from the sample. Notably, THz radiation emanates from the sample responsive to the applied THz radiation pulse as a function of one or more properties of the sample. The electric field can be evaluated to identify the one or more properties of the sample.

The THz sensor head 51, which is coupled to the THz/TDS optoelectronic device 110 via the fiber optic link 115, generates a terahertz (THz) radiation pulse at the sample location, P0, responsive to receiving the pulsed laser signal. As an example, the THz sensor 51 can be a photo-conductive emitter comprising a semiconductor material to which a voltage is applied. As an example, the Tx electrical line can serve to bias the THz sensor head 51. The semiconductor material emits a THz radiation pulse when exposed to the pulsed laser signal. Effectively, the semiconductor generates a sudden electrical current responsive to receiving the pulsed laser signal which results in the generation of the THz radiation pulse.

THz sensor 51 can be provided in a variety of known embodiments. In one embodiment, THz sensor 51 comprises a transparent crystal material that without an applied voltage emits a THz radiation pulse when exposed to the pulsed laser signal. In another embodiment, the THz sensor head 51 can comprise two electrodes patterned on gallium arsenide (GaAs) semiconductor material in the form of a dipole antenna.

The THz receiver 52 is disposed proximate to the THz sensor head 51 on the sheet material and measures the emanated THz radiation reflected from the sample location or transmitted through the sample location. As one example, the THz receiver 52 can be provided in a variety of known embodiments, such as a crystalline material arranged as a dipole antenna that becomes birefringent in the presence of the electrical field.

The scanner 120 which houses the sensor device 23 can provide a wired or wireless link to the electrical interface 175 for communicating the time-domain voltage signals (e.g. Rx electrical and Tx electrical) to the electrical interface 175. In such regard, electrical signals corresponding to the emanated THz radiation, the pulsed laser signal, and the ultra-short laser signals that are transmitted to the electrical interface 175. The electrical interface 175 produces sensory signals that are generally proportional to the electric field of the THz radiation pulses at the time an ultra-short THz signal passes through the THz receiver 52.

The controller 25 can send control signals to the THz/TDS optoelectronic device for varying the timing of the ultra-short laser pulses. More specifically, the controller 25 can vary the timing of the ultra-short pulses to sample the THz radiation pulse and construct its electric field as a function of time. That is, the controller 25 repeats the process of varying the timing of the ultra-short THz pulses while taking time domain measurements of the emanated THz radiation to construct a time-varying electric field at the sample location, P0.

The THz radiation pulse transmitted by the sensor head 51 is generally focused onto the paper 14 and is distorted by selective absorption as it passes through the paper 14, causing delays in its arrival time at the detector. By varying the time at which the ultra-short THz pulse arrives at the THz receiver 52, successive portions of the THz radiation pulse can be detected and built into a complete image of the THz radiation pulse in terms of its delay time, or time-domain. The data can then be processed by fast Fourier transform analysis in order to convert the delay time into the frequency of the terahertz signal that arrives at the THz receiver 52 as previously noted.

The signal processor 87 (see FIG. 4) which is communicatively linked to the THz receiver 52 can generate a spectrum of the sample from time domain data associated with emanated THz radiation. As an example, the signal processor 87 can perform a Fourier Transform on the received time domain data to generate the spectrum. The analyzer 88 (see FIG. 4) which is also remotely located from the process obtains a plurality of properties of the paper 14 from the spectrum during the manufacturing process. For example, the analyzer 88 can identify amplitude peaks in the spectrum or measure phase difference to identify different properties of the paper 14. The controller 25 can then control one or more aspects of the manufacturing process responsive to the sensor signals as previously described, for example, by actuating one or more control devices.

As shown in FIG. 5, THz-TDS-based measurement system 500 can be implemented in scanning or non-scanning single sided mode using fiber optic means to keep sensitive electronics of the THz/TDS optoelectronics 110 off-process (that is, outside the "wet-end" environment). In scanning mode, the sensor device 23 moves the ultra-short THz pulses along the paper. In non-scanning mode (fixed point mode), the sensor device 23 measures the paper properties at a fixed location during the paper-making process. In either mode, the result can be a combination of the primary property measurements; weight, moisture, caliper, composition and orientation all captured coincidently using the sensor 23.

As an example, the reflection scanner 120 can be placed at an exit of a third nip on a tri-nip press to take a scanning single sided THz measurement. The controller 25 can analyze a radiation spectrum that emerges from the paper, and compute one or more paper quality properties from the analysis of the radiation spectrum. For instance, the controller 25 can measure the total basis weight, water weight and caliper simultaneously at this particular location by examining peaks and phase differences in the radiation spectrum. This allows the controller 25 to accurately calculate percent solids since the basis weight and water weight are measured from the same area, or spot, of paper, P0. The controller 25 can also precisely measure paper density since both the basis weight and caliper are also measured simultaneously from the very same spot of paper, P0. It should also be noted that the scanning reflection scanner 120 can if requested remain at a fixed location to take fixed point measurements.

Figure 6:
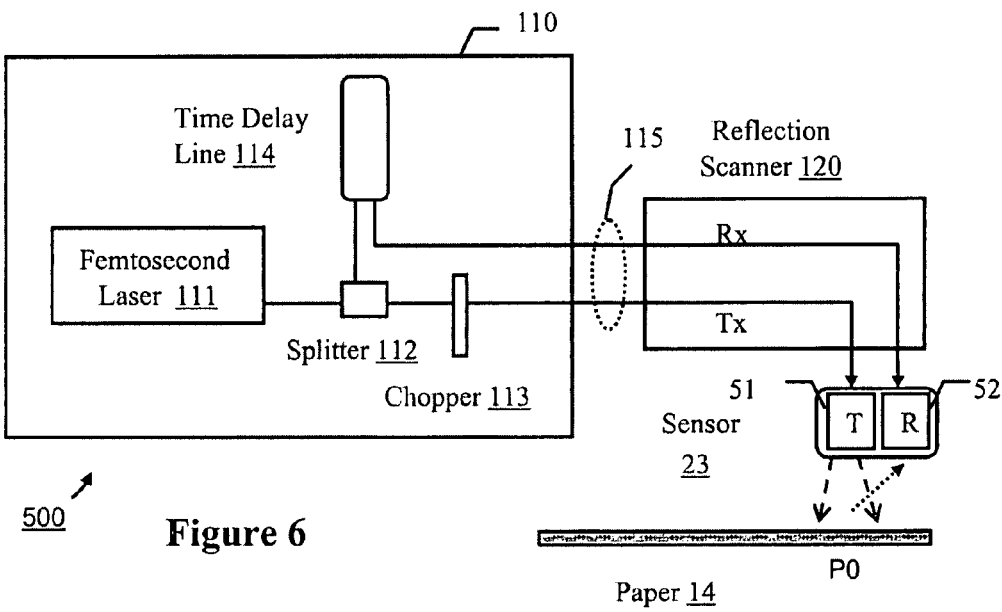
FIG. 6 is a more detailed schematic illustration of the exemplary system of FIG. 5, according to an embodiment of the present invention.

Now referring to FIG. 6 a more detailed schematic illustration of the exemplary THz-TDS-based measurement system 500 of FIG. 5 is shown. In particular, the THz/TDS optoelectronic device 110 can comprise a pulsed laser, such as a femtosecond laser 111, to produce a laser beam, and synchronization optics comprising splitter 112 to split the laser beam into a transmit beam and the ultra-short laser pulses, a chopper 113 to receive the transmitted beam (Tx) from the splitter 112 and produce the pulsed laser signal that is conveyed to the sensor head 51 through the Tx laser path of the fiber-optic cable 115 (see FIG. 5). The splitter 112 and chopper 13 structure can generate ultra-short laser pulses of light on the order of $10^{-15}$ seconds in length. Synchronization optics also includes time delay line element 114 which varies the timing of the ultra-short laser pulses and conveys the ultra-short laser pulses to the THz receiver 52 through the Rx laser path of the fiber-optic link 115. In particular, the controller 25 directs the time delay line element 114 to adjust the delay of the ultra-short laser pulse so it arrives simultaneously with the pulsed laser signal. The THz receiver 52 produces a different electrical signal depending on whether the ultra-short laser pulse arrives when an electric field of the THz radiation pulse produced by the THz sensor head 51 is low or high.

The controller 25 (See FIG. 5) analyzes multiple properties of the sample at location, P0, from the emanated THz radiation, for example, by spectral analysis. The controller 25 computes a coincident measurement comprising basis weight, moisture content, and caliper from the spectral analysis. Notably, the coincident sensor device 23 measures a plurality of paper-quality properties at the single location, P0, from the spectral analysis. Upon analyzing the measured coincident paper quality parameters, the controller 25 can predict formation errors, and adjust one or more process parameters using control device 150 to compensate for the formation errors. In such regard, the controller 25 can separate machine direction (MD) and cross direction (CD) variation measurements of the paper-making process.

Figure 7:
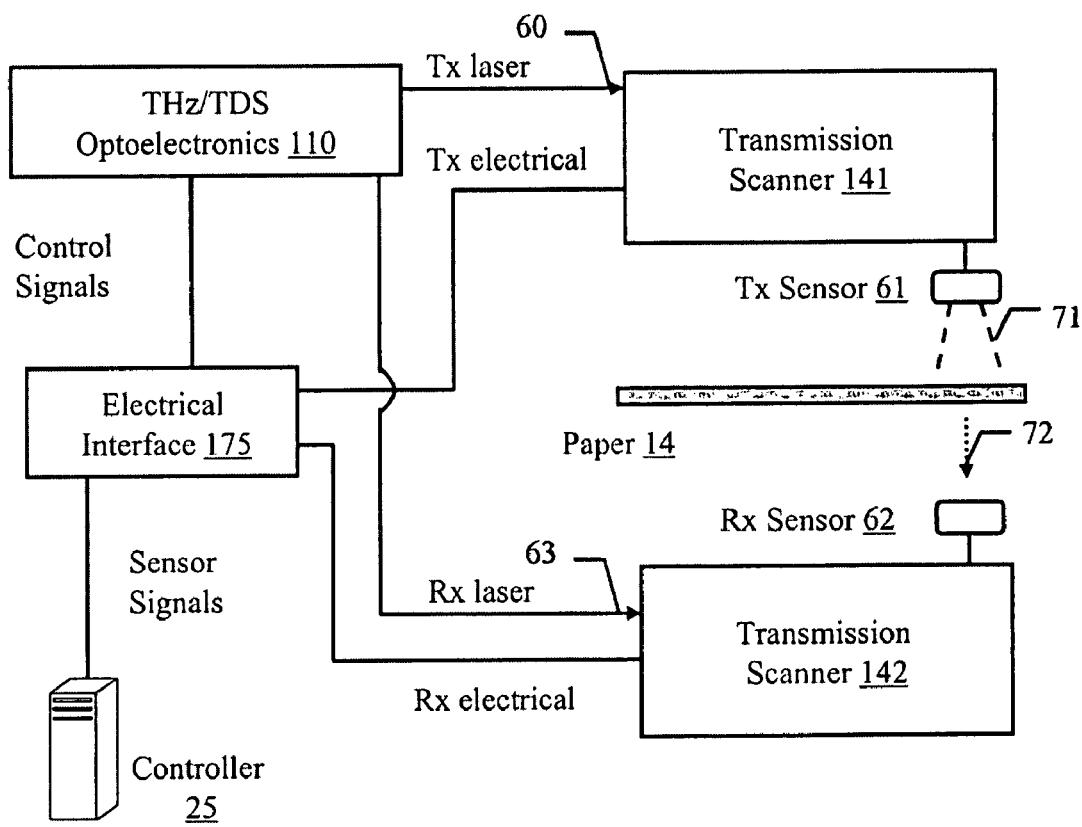
FIG. 7 is a schematic illustration of an exemplary high-speed fiber optic transmission scanning system incorporating the sensor device of FIG. 2, according to an embodiment of the present invention.

Now referring to FIG. 7 a THz-TDS-based measurement system implementing a dual-sided transmission scanner 141 is shown. Although the transmission system 700, due to the underside transmission scanner 142 takes up more space than the reflection scanner 120 (see FIG. 7), it can be placed at strategic locations within the paper-making process, for example, near the steam box 28 or a calendering stack 30 (see FIG. 3) where access to both sides of the paper 14 is provided.

The transmission scanner 141 can include the THz/TDS optoelectronics 110 which generates the pulsed laser signal 60 and the ultra-short laser signals 63 remotely from the manufacturing process. The sensor head 61 on a first side of the scanner 141 receives the pulsed laser signal 60 via the Tx laser path of the fiber optic link 115. The sensor head 61 converts the pulsed laser signal 60 to the THz radiation pulse 71 which is directed through the sheet material at sample location, P0. The THz receiver 62 on a second side of the scanner 142 receives the emanated THz radiation 72 from the sample. The THz receiver 62 also receives the series of ultra-short laser signals 63, each gated at different times, during sample measurement via the Tx laser path of the fiber optic link 115. The THz receiver 62 measures a time-domain voltage signal corresponding to the electric field of the THz radiation emanated from the sample location when the ultra-short laser signals 63 are received at the gated signal times.

The electrical signals associated with the emanated THz radiation, the pulsed laser signal, and the ultra-short laser signals following conversion to electrical signals are communicated to the electronic interface 175 via wired or wireless connection. The controller 25 which receives the sensory signals from the electrical interface 175 varies a timing of the ultra-short laser pulses to measure an electric field of the THz radiation pulse at the sample location as a function of time. As previously noted, the controller 25 generates a transmission spectrum of the sample for the THz radiation pulse from the sensory signals. The controller 25 coincidently measures a plurality of properties of the sheet material from the transmission spectrum during the manufacturing process. For example, the controller 25 computes basis weight, moisture content, and caliper of the sheet-material at the sample location from the plurality of properties.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Therefore, it is intended that the disclosure not be limited to the particular embodiment(s) disclosed as the best mode contemplated for carrying out this invention, but that the invention will include all embodiments falling within the scope of the appended claims.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims.

What is claimed is:

1. A sheet material measurement system, comprising:
   a THz generator including at least one laser source for emitting optical pulses, said optical pulses coupled to a THz emitter operable for emitting pulsed THz radiation at a first sample location on said sheet material while being processed by a manufacturing system;
   a receiver operable to receive said optical pulses and to detect reflected or transmitted THz radiation from said first sample location synchronously with said optical pulses and provide electrical detection signals;
   synchronizing optics operable to receive said optical pulses from said laser and provide said optical pulses to both said receiver and said THz emitter, and
   a controller comprising at least one processor for receiving said electrical detection signals and providing a processed electrical detection signal and an analyzer operable to determine a plurality of different sheet material properties selected from the group consisting of basis weight, moisture content, thickness, composition and fiber orientation at said first sample location from said processed electrical detection signal.

2. The system of claim 1, further comprising fiber optics, wherein said optical pulses are coupled from said laser source to at least one of said receiver and said transmitter by said fiber optics.

3. The system of claim 1, wherein said optical pulses are coupled from said laser source to at least one of said receiver and said transmitter though free space.

4. The system of claim 1, wherein said analyzer is operable to coincidently determine said plurality of different sheet material properties.

5. The system of claim 4, wherein said plurality of different sheet material properties include said basis weight, said moisture content, said thickness, said composition and said fiber orientation.

6. The system of claim 1, wherein said controller and said laser are both remotely located from said manufacturing system.

7. The system of claim 1, wherein said controller comprises a multi-variable controller.

8. The measurement system of claim 1, wherein said THz emitter and said receiver are combined in a single sensor module.

9. The system of claim 8, further comprising fiber optics, wherein said optical pulses are coupled from said laser source to said single sensor module by said fiber optics, and a scanner coupled to said single sensor module for moving said single sensor module to obtain said plurality of different sheet material properties from a second sample location.

10. The system of claim 1, wherein said receiver and said THz emitter are located on opposite sides of said sheet material, whereby said system is a transmission-based system.

11. The system of claim 1, wherein said THz emitter and said receiver are both in fixed locations during operation of said system.

12. A controlled system for forming sheet material, comprising:
a sheet material making system including a plurality of actuators;
a control system operatively coupled to said sheet material making system comprising a THz generator including at least one laser source for emitting optical pulses, said optical pulses coupled to a THz emitter operable for emitting pulsed THz radiation at a first sample location on sheet material being processed by said material masking system, a receiver operable to receive said optical pulses and to detect reflected or transmitted THz radiation from said first sample location synchronously with said optical pulses and provide electrical detection signals, synchronizing optics operable to receive said optical pulses from said laser and provide said optical pulses to both said receiver and said THz emitter, and a controller comprising at least one processor for receiving said electrical detection signals and providing a processed electrical detection signal, and an analyzer operable to determine a plurality of different sheet material properties selected from the group consisting of basis weight, moisture content, thickness, composition and fiber orientation at said first sample location from said processed electrical detection signal,
wherein said controller is operably linked to control operation of said sheet material making system using at least one of said plurality of actuators based on at least one of said plurality of different sheet material properties.

13. The system of claim 12, wherein said THz emitter and said receiver are combined in a single sensor module.

14. The system of claim 12, further comprising fiber optics, wherein said optical pulses are coupled from said laser source to at least one of said receiver and said transmitter by said fiber optics.

15. The system of claim 12, wherein said sheet material making system comprises a paper making system comprising in serial connection a press section including at least one actuator arranged to control mechanical water removal from wetstock material to begin formation of a sheet material, a dryer section including at least one actuator arranged to control evaporative drying of said sheet material, a calendering stack including at least one actuator to control compressive pressure to said sheet material, and a take-up reel for producing a continuous roll of said sheet material.

16. A method for in-situ quality control of sheet material processed by a manufacturing system, comprising the steps of:
directing THz radiation at a first sample location on material being processed by said manufacturing system;
measuring reflected radiation or transmitted radiation from said first sample location and generating electrical detection signals therefrom;
transmitting said electrical detection signals to a remotely located controller comprising at least one processor for receiving said electrical detection signals and providing a processed electrical detection signal;
determining a plurality of different sheet material properties selected from the group consisting of basis weight, moisture content, thickness, composition and fiber orientation at said first sample location from said processed electrical detection signal, and
automatically modifying at least one process parameter based on at least one of said plurality of different sheet material properties.

17. The method of claim 16, wherein said plurality of different sheet material properties are determined from coincident measuring of said reflected radiation or transmitted radiation from said first sample location.

18. The method of claim 16, wherein said THz emitter and said receiver are combined in a single sensor module, further comprising the step of scanning said single sensor module relative to said sheet material.

19. The method of claim 16, wherein said measuring comprises synchronous measuring, said synchronous measuring synchronized with optical pulses from a laser source used to generate said THz radiation, said optical pulses fiber optically coupled to a THz generator for generating said THz radiation and a receiver for said measuring said reflected radiation or transmitted radiation.

20. The method of claim 16, wherein said determining step comprises generating a time-domain spectroscopy (TDS) spectrum from said processed electrical detection signal.

* * * * *